US012662684B2

(12) United States Patent
Albertsen et al.

(10) Patent No.: US 12,662,684 B2
(45) Date of Patent: Jun. 23, 2026

(54) ENHANCING THE EFFECTIVENESS OF BLENDED REFUGE

(71) Applicant: PIONEER HI-BRED INTERNATIONAL, INC., Johnston, IA (US)

(72) Inventors: Marc C Albertsen, Grimes, IA (US); Laura Sue Higgins, Des Moines, IA (US); Mary Trimnell, West Des Moines, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 928 days.

(21) Appl. No.: 17/451,547

(22) Filed: Oct. 20, 2021

(65) Prior Publication Data

US 2022/0033843 A1     Feb. 3, 2022

Related U.S. Application Data

(63) Continuation of application No. 15/551,822, filed as application No. PCT/US2016/017107 on Feb. 9, 2016, now abandoned.

(60) Provisional application No. 62/117,685, filed on Feb. 18, 2015.

(51) Int. Cl.
| *C12N 15/82* | (2006.01) |
| *A01C 1/00* | (2006.01) |
| *A01C 21/00* | (2006.01) |

(52) U.S. Cl.
CPC ............ *C12N 15/8286* (2013.01); *A01C 1/00* (2013.01); *A01C 21/00* (2013.01)

(58) Field of Classification Search
None
See application file for complete search history.

(56) References Cited

U.S. PATENT DOCUMENTS

| | | | |
|---|---|---|---|
| 2002/0069435 A1 | 6/2002 | Kermicle et al. | |
| 2002/0104115 A1 | 8/2002 | Hoegemeyer | |
| 2010/0210460 A1 | 8/2010 | Coaldrake | |
| 2012/0137391 A1 | 5/2012 | Davis et al. | |
| 2014/0080755 A1* | 3/2014 | Heck et al. ........ | C12N 15/8218 514/4.5 |
| 2014/0366786 A1* | 12/2014 | Carroll et al. ..... | C12N 15/8265 47/58.1 FV |
| 2018/0030471 A1 | 2/2018 | Albertsen et al. | |

OTHER PUBLICATIONS

Zhang et al. (2012) Theor Appl Genet 124:459-65.*
Drury et al. (2008) J Agric Food Chem 56 4623 30.*
Drury, et al.: J Agric Food Chem, 2008, vol. 56, pp. 4623-4630.
EPA White Paper on Resistance in Lepidopteran Pests of Bacillus Thuringiensis (Bt) Plant Incorporated Protectants in the United States (2018).
Nelson: "The gametophyte factors of maize," In: Freeling M & Walbot V, eds., The Maize Handbook, Berlin (Germany): Springer-Verlag, p. 496-503.
Schwartz, "The Analysis of a Case of Cross-Sterility in Maize", P.N.A.S., vol. 36: 719-724 (1950).
Zhang, et al.: Theor Appl Genet, 2012, vol. 124, pp. 459-465.
International Search Report and Written Opinion for the International Application PCT/US16/17107 mailed Jun. 24, 2016.
Xianrong Z, "Research Progress of Maize Unidirectional Outcross Incompatibility Gene and Its Application in Maize Breeding," Maize Science, pp. 1-4. 2014.

* cited by examiner

*Primary Examiner* — Russell T Boggs

(57)     ABSTRACT

The present invention provides a seed blend comprising pesticidal seed and refuge seed, wherein plants grown from the pesticidal seed type do not pollinate or have reduced pollination of plants grown from the refuge seed type when the seed blend is planted. Methods for deploying the seed blend and for reducing cross-pollination between plants grown from the pesticidal seed and refuge seed are also provided.

29 Claims, 2 Drawing Sheets

ENHANCING THE EFFECTIVENESS OF BLENDED REFUGE

FIELD

The disclosure relates to the control of pests that cause damage to crop plants through feeding. The disclosure also relates to the management of development of pest resistance to a pesticidal agent. In particular, the disclosure relates to seed blends and methods of deploying a refuge crop accompanying a transgenic-pesticidal crop.

BACKGROUND

Transgenic maize and cotton expressing *Bacillus thuringiensis* (Bt) proteins were planted on >72 million hectares in 2013. Generally these Bt crops have been very effective against the target insect pests. However, the intensive use of Bt crops places a high selection pressure on the target pest populations increasing the potential for evolution of resistant insects. The threat of insect resistance to *Bacillus thuringiensis* (Bt) led to regulatory oversight of these transgenic crops and the adoption of a high dose/refuge strategy for planting Bt maize to combat resistance development. This strategy is based on the concept that Bt-susceptible insects produced in refuge areas will mate with the rare resistant homozygous individuals that might emerge from the Bt crop and progeny from this mating will be heterozygous and thus should be killed by the high-dose Bt plants upon a subsequent exposure. Therefore, resistance allele frequencies in field populations should remain low for a relatively longer period of time. Recently an integrated refuge seed mixture approach has been adopted by growers. This type of refuge mixes the non-Bt isoline seed directly in the bag with the traited insect control product. Upon planting, the refuge is randomly distributed throughout the field insuring that every bag of seed sold contains the required refuge. In addition, pyramided Bt maize hybrids expressing two or more Bt genes having different modes of action targeting the same pest species have been introduced. A concern in implementing the refuge-in-a-bag strategy for maize ear feeding insects is the increase in cross-pollination of maize hybrids due to the proximity of the isoline and Bt plants in the field that can cause Bt proteins to be present in refuge maize kernels in sub-lethal dosages in integrated refuge fields. These cross-pollinated ears could negatively affect survival, growth, and development of refuge insects; giving partially-resistant insects an advantage over susceptible insects, thereby potentially accelerating the development of insect resistance to the traited genes. It has recently been shown that a mixed planting of 5% refuge and 95% Bt maize containing the SmartStax® traits expressing Cry1A.105, Cry2Ab2 and Cry1F did not provide an effective refuge for corn earworm, *Helicoverpa zea* (Yang F. et al., Plos ONE 9(11); e112962 2014). Yang et al. showed that cross-pollination caused a majority (>90%) of refuge kernels to express at least one Bt protein. The contamination of Bt proteins in the refuge ears reduced neonate-to-adult survivorship of *H. zea* to only 4.6%, a reduction of 88.1% relative to larvae feeding on ears of pure non-Bt maize plantings. The limited survivors on refuge ears had lower pupal mass and took longer to develop to adults, potentially leading to the development of partially-resistant insects. Therefore, new insect resistance strategies are needed to combat insect resistance and to provide regulatory compliance.

SUMMARY

This disclosure relates to a new type of seed blend designed to eliminate or greatly reduce cross-pollination and methods for deploying the refuge crop. Relative to standard refuge practices, the present disclosure provides a refuge that results in increased survival of susceptible pests, thereby: (i) delaying the evolution of resistant pest progeny, (ii) reducing the advantage of partially resistant insects in a blended refuge and (iii) improving durability of transgenic pesticidal crops.

In one aspect, the disclosure provides a novel corn seed blend comprising (a) a first corn seed type comprising an insect resistance transgene(s) and that is free of any gametophyte factor alleles that would confer preferential fertilization; and (b) a second corn seed type comprising at least one dominant gametophyte factor allele ($Ga_x$) or transgene, where said dominant allele or transgene reduces pollination by any pollen not carrying the appropriate allele for a given gametophyte factor series. Thus, in one embodiment, plants grown from the second corn seed type are substantially to completely un-pollinated by plants grown from the first corn seed type.

In another aspect, a plant grown from the second seed type may sexually mature at a time different from a plant grown from the first seed type due to a difference in time to silk or time to mid-silk.

In a further aspect, the first corn seed type may further comprise other transgenes, such as one or more transgenes encoding a toxin effective against the same or different pest(s) for which the transgene product of the first corn seed type is effective against, and/or one or more herbicide resistance genes, and/or one or more fungicide tolerance genes.

In another aspect, a corn ear produced by plants grown from the second corn seed type exhibit a reduced number of seed comprising the transgene of the first corn seed type when compared to a control corn seed blend comprising seed types that are cross pollination compatible.

In another aspect, the ratio of the first corn seed type to the second corn seed type is from about 70:30 to about 99:1, from about 80:20 to about 97:3, or from about 90:10 to about 95:5. For instance, the ratio may be about 70:30, 71:29, 72:28, 73:27, 74:26, 75:25, 76:24, 77:23, 78:22, 79:21, 80:20, 81:19, 82:18, 83:17, 84:16, 85:15, 86:14, 87:13, 88:12, 89:11, 90:10, 91:9, 92:8, 93:7, 94:6, 95:5, 96:4, 97:3, 98:2, or 99:1. "About" when used herein in the context of the ratio of seed types in a blended refuge means±0.5%

In further aspects, the relative maturity rating for plants grown from seed of the second corn seed type may be at least 3, 4, 5, 6, 7, 8, 9, 10, or 11 days earlier or later than the relative maturity rating for plants grown from seed of the first corn seed type.

In some aspects, the first corn seed type comprises one or more transgenes encoding for *Bacillus thuringiensis* endotoxins (Bt toxin or Bt) including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, Cry72, Cry73, and Cry74 classes of δ-endotoxin genes and the *B. thuringiensis* cytolytic cyt1 and cyt2 genes. Members of these classes of *B. thuringiensis* insecticidal proteins are known to one skilled in the art (see, Crickmore, et al., "*Bacillus thuringiensis* toxin nomenclature" (2011), at lifesci.sussex.ac.uk/ home/Neil_Crickmore/Bt/ which can be accessed on the world-wide web using the "www" prefix).

In some aspects, the first corn seed type comprises one or more transgenes encoding for pesticidal products selected from the group consisting of VIP3A, VIP3Aa, Cry1A.105, Cry2Ab, Cry1F, Cry1A, Cry1Ab, Cry1Ac, Cry34/35, Cry34/35Ab1, Cry34Ab1, Cry35Ab1, Cry3A, mCry3A, eCry3.1Ab, Cry3Bb, Dv49 dsRNA, and Dv_Snf7o.

In still further aspects, the first corn seed type comprises an event selected from the group consisting of DP-186165-2, DP-186169-6, DP-187156-3, DP 4114, MIR162, MIR 604, Bt 176, TC1507, DAS-06275-8, DAS-59122-7, Bt11, 5307, MON810, MON89034, MON88017, ZM_S295399, MON87411, MON853, and MON863.

In some aspects, the first corn seed type comprises one or more transgenes encoding for one or more pesticidal proteins. In addition to *Bacillus thuringiensis*, pesticidal proteins have been isolated from organisms including, for example, other *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Pechy-Tarr, (2008) *Environmental Microbiology* 10:2368-2386; GenBank Accession No. EU400157); from *Pseudomonas Taiwanensis* (Liu, et al., (2010) *J. Agric. Food Chem.*, 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US patent Publication US20140274885 or PCT Patent Publication WO2014/150914; a PIP-47 polypeptide of PCT Serial Number PCT/US14/51063, a PIP-72 polypeptide of PCT Serial Number PCT/US14/55128.

In another aspect, the disclosure provides a field of plants grown from the corn seed blend of the present disclosure.

In still another aspect the disclosure provides a method of reducing the incidence of pollination between plants grown from different seed types in a corn seed blend, the method comprising providing a corn seed blend comprising (i) a first corn seed type comprising at least one insect resistance transgene and (ii) a second corn seed type comprising at least one dominant gametophyte factor allele and that lacks the insect resistance transgene, where the dominant gametophyte factor allele reduces pollination by recessive gametophyte factor pollen characteristic of corn seed comprising insect resistance transgenes.

In some aspects, plants grown from the second corn seed type are substantially unpollinated by plants grown from the first corn seed type.

In another aspect, a corn ear produced by plants grown from the second corn seed type exhibit a reduced number of seed comprising the insect resistance transgene when compared to a control corn seed blend comprising seed types that are cross pollination compatible. In yet another embodiment, the ratio of seed of the first corn seed type to seed of the second corn seed type in the seed blend is selected from the group consisting of from about 70:30 to about 99:1, from about 80:20 to about 97:3, and from about 90:10 to about 95:5.

In still another aspect, the pollen shed period of plants grown from seed of the first seed type does not substantially overlap with the mid-silk timing of plants grown from seed of the second seed type.

In some aspects the insect pest is a Lepidopteran species. In some embodiments the insect pest is a corn ear feeding insect. In some embodiments the insect pest is in the Family Noctuidae or Crambidae. In some embodiments the insect pest is in the Family Noctuidae. In some embodiments the insect pest is in the Family Crambidae. In some embodiments the insect pest is corn earworm (CEW; Noctuidae: *Helicoverpa zea*), western bean cutworm (WBC; Noctuidae: *Striacosta albicosta*), fall armyworm (FAW; Noctuidae: *Spodoptera frugiperda* (Smith)), European corn borer (ECB; Crambidae: *Ostrinia nubilalis*), variegated cutworm (VC; Noctuidae: *Peridroma saucia* (Hübner))

In an additional aspect, the pesticidal agent is active against *Helicoverpa zea* and the reduction occurs at the tip portion of the corn ears.

In other aspects, the pesticidal agent is active against *Helicoverpa zea* and reduces insect feeding.

In another aspect, the disclosure provides a method of reducing the incidence of pollination between plants grown from different seed types in a corn seed blend comprising applying a treatment to plants grown from the corn seed blend, where (a) plants grown from the first corn seed type comprise a gene or gene product that interacts with the treatment and plants grown from the second corn seed type lack the gene or gene product, and where the interaction delays or accelerates time to reproductive maturity of plants; or (b) plants grown from the second corn seed type comprise a gene or gene product that interacts with the treatment and plants grown from the first corn seed type lack the gene or gene product, and where the interaction delays or accelerates time to reproductive maturity of plants.

In a further aspect, the disclosure provides a method for enabling compliance with government regulations for planting a refuge crop with or alongside of an insecticidal transgenic crop, where the refuge crop comprises at least one dominant gametophyte factor allele and lacks the insect resistance transgene, where the dominant gametophyte factor allele reduces pollination by recessive gametophyte factor-containing pollen.

In a still further aspect, the disclosure provides a method for enabling compliance with government regulations for planting a refuge crop with or alongside of an insecticidal transgenic crop, where the refuge crop further comprises a reproductive maturity rating that is different from the reproductive maturity rating of the insect resistance transgene crop, where the refuge reproductive maturity rating differs from the insecticidal transgenic crop sexual maturity rating by at least 3 days.

5

6

Figure 3:
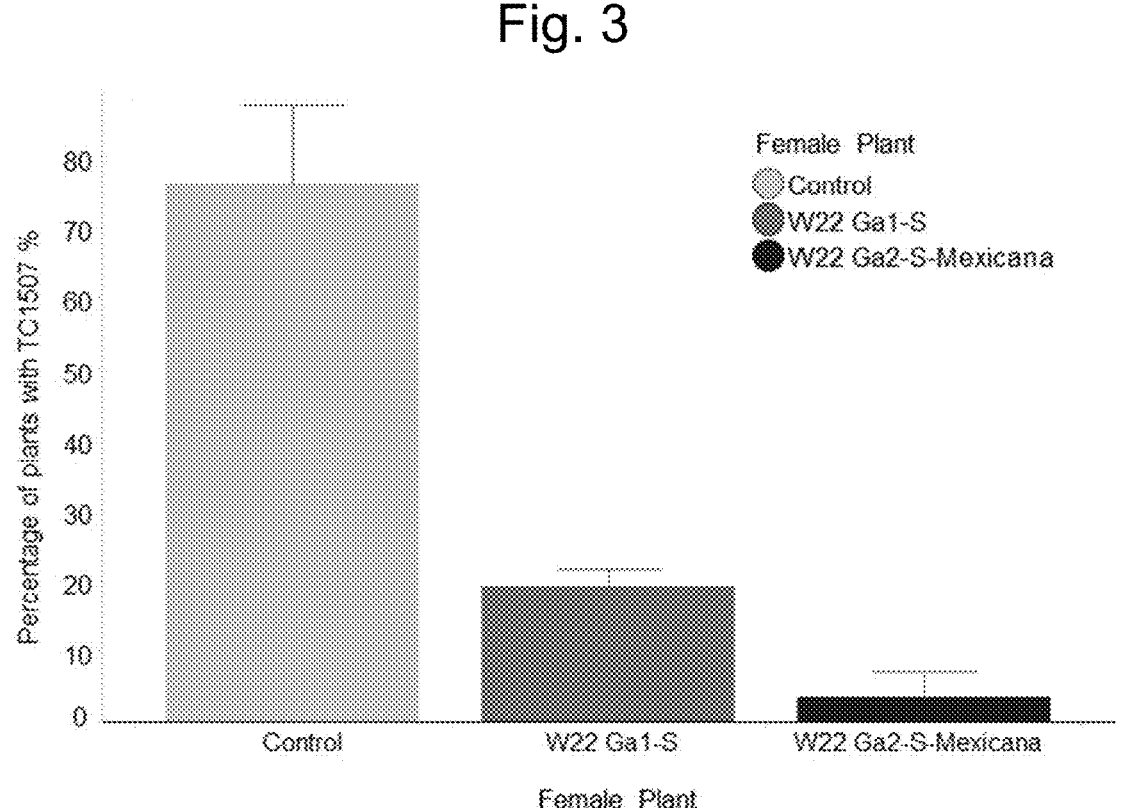

FIG. 3 shows the percentage of plants that were products of cross-pollination as indicated by the presence of the TC1507 event.

DETAILED DESCRIPTION

The present disclosure provides compositions and methods for reducing the risk of insect resistance development in cultivated insecticidal crops. In particular, the disclosure relates to improved insect resistance management practices, such as seed blends, and improved methods for deploying a crop refuge. Such improvements may be provided, for instance, by reducing cross-pollination of refuge crop plants by transgenic pesticidal crop plants in a refuge-integrated field.

Insect Resistance Management (IRM) reduces the likelihood of development of resistance to one or more recombinant insecticidal trait that is present within a recombinant plant. One approach for achieving resistance management is through a seed mix or seed blend refuge composition, e.g., refuge-in-a-bag (RIB). However, cross-pollination of a refuge crop plant by transgene-containing pollen from a transgenic insecticidal crop plant can result in production of progeny seed on the refuge crop plants expressing the insect resistance transgene(s). Such insecticidal trait incorporated progeny seed produced on refuge plants may impact the survivorship of susceptible pests that feed upon the seed, thus diminishing the efficiency of this management methodology to delay the evolution of pesticide resistant pests.

Reduction of the cross-pollination of refuge crop plants by transgenic insecticidal crop plants may therefore increase the production of susceptible insects in the refuge plant population of a field. In one embodiment, the present disclosure therefore provides a method of reducing cross-pollination of a refuge crop plant by transgenic insecticidal crop plants. Such reduction in cross-pollination may, for instance, be a reduction in cross-pollination of an individual refuge plant by an individual transgenic insecticidal plant, when both plants are grown from a seed blend. Such reduction in pollination may also be a reduction in cross-pollination of a population of refuge plants by a population of transgenic insecticidal plants.

The disclosure provides a method for deploying refuge crops comprising planting in a field a seed blend comprising seed of a transgenic insecticidal crop population and seed of a refuge crop population that is cross-pollination incompatible with the transgenic insecticidal crop population.

The interaction between pollen and stigmas directs reproductive compatibility in flowering plants. Some varieties of popcorn will not set seed when pollinated by dent or flint maize strains, but no difficulty is experienced in making the reciprocal cross. Cross-incompatibility factor genes known as gametophyte factors when present in the silks discriminate against pollen lacking the compatible allele. One example of the genetic basis of this non-reciprocal cross-incompatibility is a multiple allelic series at the Ga1 locus on chromosome 4 of maize such that Ga1/Ga1 plants will not set seed when pollinated with ga1 (typical field corn) pollen. The Chinese popcorn strain SDGa25 is one example of a line that carries the strongest allele of Ga1 (Ga1-s) (Zhang H. et al., *Theo Applied Genet* 124:459-465, 2012). Another gametophyte factor, Tcb1, was identified from teosinte on chromosome 4 and was named "teosinte crossing barrier-1" (Tcb1). Tsb1-s, the strongest allele of Tcb1, prevents teosinte (Tcb1-sTcb1-s) from being fertilized by *Zea mays* (tcb1tcb1) while promoting its own propagation (Evans M S et al, *Theo Applied Genet* 103:259-265, 2001). More recently the sexual incompatibility gene Ga2 was identified on chromosome 5, which is different from those previously described (Kermicle J L, J. of *Heredity* 101:737-749, 2010). Cross-incompatibility factor genes have been used in maize breeding to develop non-genetically modified maize varieties that will not accept pollen from genetically modified maize varieties, thus preventing unintended introduction of transgenes into the non-genetically modified maize varieties (U.S. Pat. Nos. 6,875,905; 7,074,984).

In one embodiment, the disclosure provides a method for deploying refuge crops comprising planting in a field a seed blend comprising seed of a transgenic insecticidal crop population and seed of a refuge crop population comprising a dominant gametophyte factor allele and that lacks the insect resistance transgene, where the dominant gametophyte factor allele reduces pollination by recessive gametophyte factor containing pollen. In some embodiments the dominant gametophyte factor allele is Ga1-s, Ga2-s, and/or Tcb1-s, or a functionally equivalent transgene.

In some embodiments, methods are provided for deploying a refuge crop comprising planting in a field a seed blend comprising seed of a transgenic insecticidal crop population and seed of a refuge crop population comprising a dominant gametophyte factor allele and that lacks the insect resistance transgene, and further the transgenic insecticidal crop population and refuge crop population reach reproductive maturity at different times in the field. For instance, plants of the transgenic insecticidal crop population may reproductively mature relatively earlier, relatively later, or relatively earlier and later, than plants of the refuge crop population. Such a seed blend can be described to have "differential sexual maturity ratings" between the two seed types. Plants in the transgenic insecticidal crop population and refuge population reaching reproductive maturity at different times may, in one embodiment, physiologically mature at the same time or may physiologically mature at a relatively different time, such as relatively earlier, relatively later, or relatively earlier and later.

Relative maturing ratings, e.g., time to reproductive maturity or physiological maturity of a plant species, can be predicted to varying accuracy depending on plant species and knowledge of parental maturing rates. Maturing ratings relative to female and male parts of plant species can also be predicted with precision, especially with highly cultivated crop species such as field corn.

In certain embodiments, the transgenic insecticidal seed and the refuge seed are provided as a seed mixture or seed blend. The disclosure therefore provides a seed mixture, a seed blend, or a refuge-in-a bag. Seeds in such a mixture may be planted to produce an integrated-refuge field. The disclosure therefore further provides a refuge-integrated field resulting from the deployment seed mixtures or seed blends according to the disclosure.

An integrated-refuge field planted in accordance with the present disclosure may result in a population of refuge crop plants that is cross-pollination incompatible with the population of transgenic insecticidal crop plants deployed therewith. Developing progeny seed produced on the refuge crop may therefore be substantially pollinated (self- and/or cross-pollinated) by the refuge crop and substantially unpollinated by the transgenic insecticidal crop. Therefore, compared to a refuge-integrated field deployed from a standard refuge seed blend where refuge crops and transgenic insecticidal crops can cross pollinate, the refuge-integrated field in accordance with the present disclosure may exhibit a reduction in cross-pollination of refuge plants by transgenic insecticidal plants, thereby increasing the surviving population of susceptible insects feeding on the progeny seed of refuge plants.

In another embodiment, the reduction in cross-pollination provided by the present disclosure can result in a spatially relevant reduction of transgene transfer in a kernel assemblage, such as an ear of corn. For example, the cross pollination incompatibility of seeds in the blend may provide that, if transgene transfer due to cross-pollination occurs at all, it is limited to a particular spatial orientation on the resulting kernel assemblage, such as a location on the assemblage away from insect larvae feeding sites. For instance, in corn fields *Helicoverpa zea* (corn earworm, CEW) typically start feeding at the tip or stalk distal portion of a corn ear. Therefore, a reduction of cross-pollination may result in corn ears on refuge plants that do not comprise corn kernels containing the transgene on the distal portion, or tip of the ear, thus resulting in increased survival of susceptible CEW. Similarly, a reduction of cross-pollination resulting in corn ears on refuge plants with corn kernels not containing the transgene on the bottom portion of the ear, or the portion proximal to the stalk, can result in susceptible corn borer (*Ostrinia nubilalis*) or fall armyworm (*Spodoptera frugiperda*) survival.

Seed blends in accordance with the present disclosure comprise at least a first seed, which contains at least an insect resistance transgene, and at least one type of cross-pollination incompatible refuge plant seed. The refuge plant seed can be uniform in nature, in that it is composed of a single type of seed from a single variety of plant, or can be non-uniform in nature and consist of two or more varieties of plant. In one embodiment, the refuge seed is similar in variety (or agronomic characteristics) to the first transgenic crop seed. In another embodiment, the refuge seed is of a variety that is rated to reach reproductive maturity at a different respective time in the field than that of the transgenic insecticidal crop seed.

The refuge seed can be non-transgenic or can be transgenic. A refuge seed that is a transgenic seed can contain any transgene so long as it is not the insect resistance transgene that is present in the first transgenic crop seed. In certain embodiments, the transgene products in the transgenic refuge seed have insecticidal activity against different pests or against the same pests, but by a different mode of action, than the transgene products in the insect resistance transgene crop seed. In other embodiments, the transgene in a transgenic refuge seed is one or more insecticidal genes, one or more herbicide tolerance genes, and one or more fungicide tolerance genes, a fragment of an insect gene, or the like or a combination thereof. Refuge seeds may be grown into plants that act as a refuge for pests that either feed directly on a particular crop species, or other pests, the presence of which within the local proximity of a particular crop species, results in the damage, decrease in viability, infertility, or decrease in yield of a crop produced from such crop species.

In various embodiments, the contribution of refuge crop seed to the seed mixture or seed blend can be measured by percentage weight or count of refuge seed to total weight or count of the seed mixture. Seed mixtures in accordance with the present disclosure for deployment in a field may comprise from about 1 to about 50% refuge crop seed, from about 1% to about 10% refuge crop seed, or from about 5% to about 10% refuge crop seed. Refuge seed contribution can therefore be about 50%, 45%, 40%, 35%, 31%, 30%, 29%, 28%, 27%, 26%, 25%, 24%, 23%, 22%, 21%, 20%, 19%, 18%, 17%, 16%, 15%, 14.5%, 14%, 13%, 12%, 11%, 10%, 9%, 8%, 7%, 6%, 5%, 4%, 3%, 2%, or 1% total weight or count of the seed mixture. That is, the insect resistance transgene crop seed might comprise about 50%, 55%, 60%, 65%, 70%, 75%, 80%, 85%, 85.5%, 90%, 95% or up to about 99% of the seed mixture. The respective insect resistance transgene crop:refuge ratio (ratio of insect resistance transgene seed to refuge seed) in seed mixtures of the present disclosure may be about 50:50 to about 99:1, about 70:30 to about 99:1, about 80:20 to about 97:3, or about 90:10 to about 95:5, and any integer or fraction ratio in between, for example, about 50:50, 55:45, 60:40, 65:34, 70:30, 75:25, 80:20, 85:15, 85.5:14.5, 90:10, 95:5, 97:3, or 99:1. "About" when used in the context of the ratio of seed types in a blended refuge means±0.5%.

In one embodiment, the plant species of the insect resistance transgene crop and refuge crop may be of the seed-bearing type. In other embodiments these plants may be capable of harboring an insect resistance transgene. For instance, the plants may be selected from the group consisting of maize, corn, field corn, sweet corn, cotton, canola, wheat, rice, alfalfa, tobacco, sunflower, coffee species, tea species, grapes, plum, papaya, squash, flax, or tree species (poplar, aspen, sweetgum, eucalyptus, or spruce). In yet another embodiment, the plants may be capable of being subject to infestation and damage by a pest against which the insect resistance transgene is pesticidal. In certain embodiments, plants of the present disclosure are protected against pests that contain in their diet parts of such plants, such as the developing embryos of the plant, e.g., maize silks, maize ears, corn kernels, soybeans, cotton seed, or any crop plant grown as a hybrid.

Substantially unpollinated, as used herein can refer to a seed assemblage produced by a refuge crop that exhibits less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% or less of its kernels or seed having the transgene responsible for the insecticidal activity.

A measurable reduction in cross-pollination between insect resistance transgene crop and refuge crop plants grown from a seed blend of the present disclosure, as compared to that of a seed blend in which the insect resistance transgene crop and refuge crop plants are cross pollination compatible will further delay insect resistance development. The reduction in number of insect resistance transgene kernels in the kernel assemblage of refuge plants of the present disclosure as compared to those on refuge plants grown from a standard seed blend comprising insect resistance transgene crop and refuge crop seed that are cross pollination compatible can be described in terms of fold reduction. This reduction can be, for example, a 1.05-fold, or 1.10-fold, or 1.18-fold, or 1.25-fold, or 1.30-fold, or 1.40-fold, or 1.50-fold, or 1.70-fold, or 1.80-fold, or 2.0-fold, or any fold greater than one (1).

For example, plants grown from a standard seed blend comprising an insect resistance transgene crop and refuge crop seed that are cross pollination compatible can exhibit an average 75% transgenic insecticidal kernels on a refuge kernel assemblage, and plants grown from a seed blend in accordance with the present disclosure can exhibit an average 50% transgenic insecticidal kernels on a refuge kernel assemblage; which is equivalent to a 1.5-fold reduction in pollination of refuge plants by transgenic insecticidal plants.

In another embodiment, a refuge kernel assemblage produced from a standard seed blend comprising transgenic insecticidal crop and refuge crop seed that are cross pollination compatible can exhibit 25% transgenic insecticidal kernels on the refuge kernel assemblage, and a refuge kernel assemblage produced from a seed blend in accordance with the present disclosure can exhibit 5% transgenic insecticidal kernels on the refuge kernel assemblage; which is equivalent to a 5-fold reduction in pollination of refuge plants by transgenic insecticidal plants.

In another embodiment, the transgenic insecticidal crop of the present disclosure may further harbor a gene or gene product that interacts with the treatment resulting in a delay or acceleration in the time to reproductive maturity, while the refuge crop lacks the gene or gene product. Alternatively, the refuge crop may comprise the gene or gene product, while the transgenic insecticidal crop lacks the gene or gene product. In various embodiments, the gene or gene product may be a transgene encoding an herbicide tolerant protein product that protects the crop from reproductive delay due to herbicide treatment. Alternatively, the gene or gene product may be an endogenous plant reproductive pathway gene that is sensitive to RNA treatment, (e.g., down-regulating a maize flowering time gene such as but not limited to "delayed flowering1" (dlf1) or "floral transition at the meristem1" (ftm1), which are required for timely promotion of the floral transition).

In another embodiment, the relative difference in reproductive maturity between the transgenic insecticidal crop seed and the refuge crop seed may be a result of treating either the transgenic insecticidal crop seed or the refuge crop seed with a formulation to delay or accelerate plant growth rate to reproductive maturity. In one embodiment, treatment with the formulation may occur prior to planting, such as a seed treatment, or may occur after planting the seed, such as a soil drench or foliar spray. In certain embodiments, such treatment formulations that delay developmental timing may include plant hormone growth regulators, e.g., abscisic acid (ABA) and BIONIK (a formulation of 25% s-abscisic acid (s-ABA)).

Definitions

Unless defined otherwise, all technical and scientific terms used herein have the same meaning as commonly understood by one of ordinary skill in the art to which this disclosure belongs. The inventors do not intend to be limited to an example or to a variation of practice.

The term "field" refers to a cultivated expanse of land that a farmer uses to grow a crop species. A field ranges in size depending on crop species and purpose. In one embodiment, a maize field can include rows. Row spacing in a maize field can vary, e.g., from 15 inches to 22 inches to about 30 inches. Maize field rows can be planted at various rates, e.g., from about 12,000, 18,000, 24,000, 30,000, 34,000, 36,000, to 50,000 seed per acre; and can be planted at various lengths.

As used herein, the term "insect resistance transgene product", can mean a "pesticide", a "Bt" or "Bt polypeptide" where the plant protectant is a protein, or a variant thereof, derived from *Bacillus thuringiensis*, a "non-Bt" or "non-Bt polypeptide", where the plant protectant is a protein, or a variant thereof, derived from a bacterium other than *Bacillus thuringiensis* or a plant, particularly from a fern or other primitive plant, or "RNA" where the plant protectant is an RNA molecule, particularly a RNAi or dsRNA. Transgenic insecticidal products can be expressed from a transgenic event that comprises a transgene encoding the transgenic insect resistance trait.

An "integrated-refuge" field as used herein refers to a field containing a population of transgenic insecticidal plants and a population of refuge plants. Transgenic insecticidal and refuge populations can be planted from a seed blend, such as a "refuge-in-a-bag" seed blend. Such a field may include a first population crop that harbors one or more transgenic insect resistance traits with pesticidal activity against a pest or a number of pests of the crop species, and a second population refuge crop that is not pesticidal against the pest or the number of pests of the crop species or is insecticidal against the same pest or number of pests, but through a different mode of action. As used herein, the first population transgenic insecticidal crop is grown from a "first seed type", "pesticidal seed" or "transgenic insect resistance seed", and the second population refuge crop is grown from a "second seed type" or "refuge seed".

As used herein, the term "refuge" includes an isolated plant or plant population; including the plant parts, such as the seed, developing seed, or seed assemblage of the isolated refuge plant or refuge plant population. The refuge crop (plant population, isolated plant, or plant parts) functions as a dietary refuge for pest(s) under transgenic insecticidal control by nearby plants or plant parts comprising the transgenic insecticidal trait.

As used herein, the term "relative maturity rating" (RM) denotes the expected number of days after planting for a crop species to reach physiological maturity. For example, in maize crop species, crop varieties that share the same RM are rated to reach kernel black layer formation at about the same time and thus will typically be ready for ear harvest at the same time.

As used herein, the terms "reproductive maturity" and "sexual maturity" are used interchangeably. The terms "reproductive maturity rating" (RpM) and "sexual maturity rating" refer to the expected number of days after planting for a crop species to produce male or female reproductive structures, such as tassels and ears, thereby reaching reproductive or sexual maturity. In hybrid corn seed production, RpM is predicted based on the observed parental developmental timing of reproductive tissue. RpM can be predicted precisely, for example, to within a 3 day range for a crop population of commercial hybrid seed. Plants grown from hybrid seed rated to reproductively mature at the same time can be expected to reproductively mature contemporaneously in the field. As used herein, when referring to a crop population of more than one plant grown in a field, the term "contemporaneous" means "substantially at the same time."

As used herein, the term "harboring" means "comprising", "having", or "transgenic for", that is, a plant or plant cell harboring a transgene, Bt, or gene, refers to a plant or plant cell that comprises, or is transgenic for, the transgene, Bt, or gene.

As used herein, plants from the "same species" refers to seed-bearing plants which are reproductively compatible, that is, permitting breeding between plants of the species, including wild species.

As used herein, the tip of a corn ear can be identified when the ear is still attached to the stalk as the stalk distal portion of the corn ear. When unattached, the tip of a corn ear can be identified as the butt distal portion of the corn ear. In certain embodiments, the tip of the corn ear can comprise the stalk distal ½, ⅓, ⅕, ⅒, ⅟₂₀ of the ear.

The term "deploying" in the context of a field, may optionally include, e.g., preparing soil, treating seed, imaging seed, mixing seed, blending seed, planting seed, growing plants from the seed, applying water, fertilizing, applying plant protectants such as pesticides and fungicides, applying herbicides, applying desiccants or defoliants, and drying down for harvest of the crop. As used herein, "planting" seed includes "growing" plants from the seed. Unless otherwise noted, the rationales to performing such steps and the order in which they are performed would be known by one of ordinary skill in the art, e.g., a farmer.

EXAMPLES

Example 1—Assessment of Cross Pollination of Ga$_x$ Mutant Lines by Bt Inbred Lines This example illustrates a method to assess the refuge potential of a refuge plant population comprising a dominant gametophyte factor allele interplanted with a Bt transgene plant population in a field comprising a recessive gametophyte factor allele, where the Bt transgene targets a pest that feeds on the developing progeny seeds in the field. To evaluate whether the specific gametophyte factor being tested would prevent pollination by elite inbred lines, and by inference hybrid lines, having a Bt transgene but without a compatible gametophyte factor allele, hybridization experiments were conducted in a test plot. Five gametophyte factor-containing lines, four dominant and one recessive, and nine Bt inbred lines that were recessive for the gametophyte factors being evaluated, and that covered a broad range of predicted pollen shed, were used in the experiment. Each of the gametophyte factor lines were validated for the gametophyte factor being tested. The entries in the experiment were completely randomized. The experiment was planted using a single kernel planter (SKP) which allowed for each plant to be identified as its own plot. There were a total of 62 reps for each entry. Overall, the gametophyte factor test plots (and therefore plants) being tested made up 5% of the total plants in the experiment. The gametophyte factor test plants were de-tasseled so that any seeds that might form would be the result of pollination with the Bt inbred lines.

Seed set results at harvest are summarized in Table 1. All ears from the gametophyte factor containing lines were harvested and identified individually by plot. The ears were scored as having "0 Kernels Produced", "Few Kernels Produced", "Scattered Kernels" or "Full Ears". There were some missing values because of missing plants (no seed germination) or because of a plant that could not be scored (e.g., a barren plant that did not produce an ear).

None of the lines showed 100% of the ears without kernels. As expected, the A632 line with a recessive ga1 allele showed nearly all the ears produced had full seed set. Thirty-eight of the 40 ears produced had full seed set. The ga1 allele of this line was compatible with the known ga1 composition of the Bt-containing lines. In contrast, the W22 Ga2-s-*Mexicana* line showed only two of 52 totals ears that fell into the "Few Kernels Produced" category. Fifty of the 52 ears produced did not have any kernels. Although one line with the Ga1-S allele had extremely poor germination, a W22 line with the same allele showed reasonable suitability for blocking pollination by ga1 pollen. Only one of 54 ears was fully pollinated. The rest showed 2, 41, and 10 ears in the 'O,' 'Few', and 'Scattered Kernel' categories, which is still a significant reduction in seed set compared with the line with the compatible gametophyte factor (ga1).

TABLE 1

| | 0 Kernels Produced | Few Kernels Produced | Scattered Kernels | Full Ears | Missing Values |
|---|---|---|---|---|---|
| A632 ga1 su1)X | 1 | 1 | 0 | 38 | 22 |
| Ga1-S y1)X | 0 | 0 | 1 | 0 | 61 |
| W22 Ga1-S)X | 2 | 41 | 10 | 1 | 8 |
| W22 Ga2-S-Mexicana)X | 50 | 2 | 0 | 0 | 10 |
| W22 Ga2-S-Parviglumis)X | 5 | 31 | 16 | 0 | 10 |
| Total | 58 | 75 | 27 | 39 | 111 |

Example 2—Assessment of Maize Seedlings Originating from Kernels Resulting from Cross-Pollination of Ga$_x$ Mutant Lines by Bt Inbred Lines Test Substance Description and Origin This example illustrates a method for verifying how many kernels on GA$_x$ refuge plant ears were fertilized by ga$_x$ pollen from Bt event plants using glufosinate spray on maize seedlings originating from kernels from non-Bt refuge plants blended with Bt event plants, which are glufosinate resistant.
Test Substance Description and Origin Test substances were maize seedlings from kernels of refuge plants, containing the gametophyte factors listed in Table 2, blended with TC1507 event (see for example: U.S. Pat. Nos. 7,288,643; 7,417,132; 7,435,807; 7,449,564; 7,514,544; 7,989,607; and 8,901,378) inbred lines. The maize seedlings were originated from 2 different Ga mutant lines, W22 Ga1-S and W22 Ga2-S-*Mexicana*. These lines were selected as the best performing in Example 1 by producing the least amount of seed in the presence of pollinators with a range of flowering times. Seven different TC1507 event inbred lines with a broad range of pollen shed and a control W22 inbred line (W22 r-sc-m3 P-wr) were used. The experiment was completely randomized and utilized the single kernel planter, allowing each plant to have a unique plot within the field. Overall, the Ga plants made up 5% of the plants in the experiment. There were a total of 62 replicates for each entry. Plants were allowed to open pollinate in the field.
Kernel Numbers on Ears Ears were harvested, shelled, and kernel counts were taken as listed in Table 2.

TABLE 2

| Line | Total Number of Ears | Average Number of Kernels | Total Number of Kernels |
|---|---|---|---|
| W22 Ga1-S | 60 | 92 | 5544 |
| W22 Ga2-S-Mexicana | 34 | 3 | 83 |
| W22 r-sc-m3 P-wr (control) | 5 | 361 | 1804 |
| Grand Total | 99 | 77 | 7431 |

Figure 1:
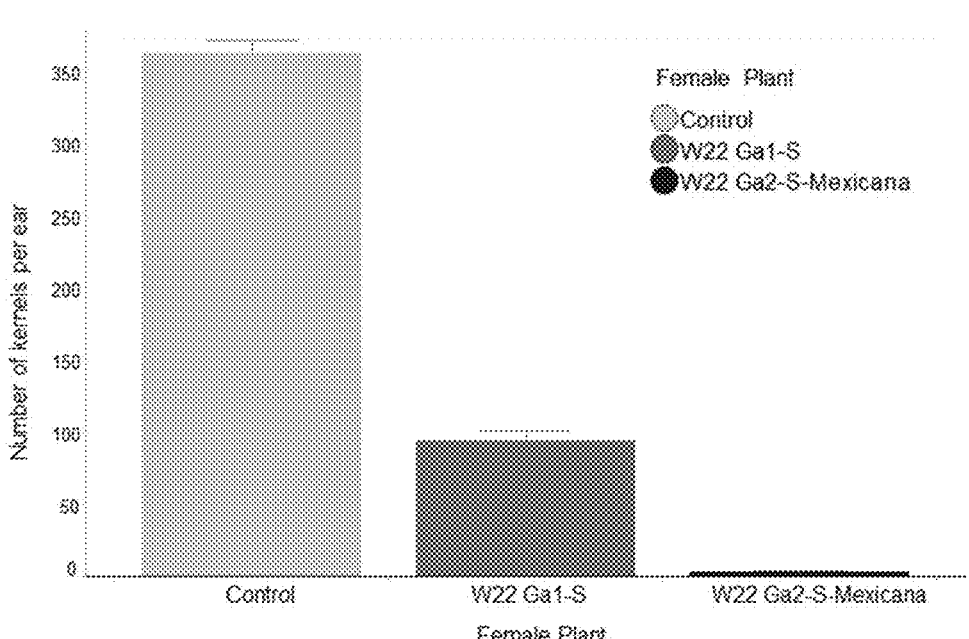
FIG. 1 shows the mean number of kernels per ear of plants containing ga$_x$ silks (control) and Ga$_x$ silks from 2 Ga$_x$ lines, W22 Ga1-S and W22 Ga2-S-*Mexicana*.

The mean number of kernels produced per ear is shown in FIG. 1. The mean number of kernels on control plants containing ga$_x$ pollen (W22 r-sc-m3 P-wr) was 362.8 kernels per ear while the mean number of kernels produced on ears of GA$_x$ plants were 94.1 (W22 Ga1-S) and 3.1 (W22 Ga2-S-*Mexicana*) kernels per ear. These results indicated that GA lines W22 Ga1-S and W22 Ga2-S-*Mexicana* produced 74 and 99%, respectively, less kernels per ear than control plants (W22 r-sc-m3 P-wr) in this particular experiment.

Germination of Kernels

Figure 2:
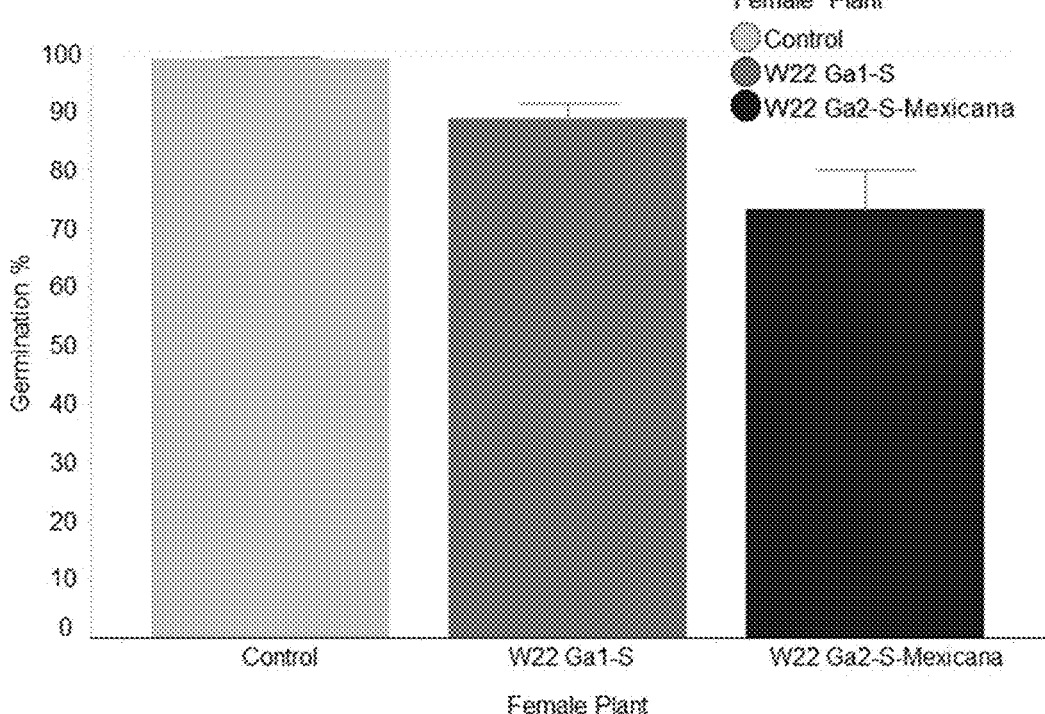
FIG. 2 shows the mean germination of kernels per ear of ga$_x$ plants (control) and Ga$_x$ plants from 2 Ga$_x$ mutant lines, W22 Ga1-S and W22 Ga2-S-*Mexicana*.

The kernels were germinated and totaled. The mean germination of kernels per ear is shown in FIG. 2. The mean germination of kernels from control plants (W22 r-sc-m3 P-wr) was 99.2%, while the mean germination of kernels per ear of Ga$_x$ plants were 88.7% (W22 Ga1-S) and 73.3% (W22 Ga2-S-*Mexicana*). These results indicated that kernels of the inbred by Ga$_x$ lines tested in this experiment (W22 Ga1-S and W22 Ga2-S-*Mexicana*) germinated 10.5% and 25.9%, respectively, less than kernels of control plants (W22 r-sc-m3 P-wr).

Kernels Developed from Cross Pollination with Ga Pollen

Seedlings were sprayed with glufosinate at rate of 6.43 L/ha. Plants that exhibited injury by the glufosinate were considered those that resulted from pollination with GA$_x$ pollen from refuge plants rather than the ga$_x$ pollen from TC1507 plants. Plants that did not exhibit symptoms of glufosinate injury were considered those that were pollinated by ga$_x$ pollen from TC1507 plants. The percentage of plants (kernels) with the event TC1507 is shown in FIG. 3. On ears of control plants (W22 r-sc-m3 P-wr), the percentage of kernels containing the event TC1507 indicates that the natural rate of cross-pollination for this control in the trial was approximately 76%. The percentage of kernels resulting from pollination with the event TC1507 was reduced on ears of GA plants to 19.1% (W22 Ga1-S) and 3.6% (W22 Ga2-S-*Mexicana*). These results indicate that, with the inbred by gametophyte factor combinations used in this experiment, Ga lines W22 Ga1-S and W22 Ga2-S-*Mexicana* reduced cross-pollination by lines containing TC1507 by approximately 57% and 72%, respectively.

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, such as different combinations of inbred lines and hybrids with different gametophyte factors, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. A corn seed blend comprising:
   (a) a first corn seed type comprising an insect resistance transgene and a recessive gametophyte factor allele; and
   (b) a second corn seed type comprising a dominant gametophyte factor allele lacking the insect resistance transgene, wherein the dominant gametophyte factor allele reduces pollination by pollen carrying the recessive gametophyte factor allele.

2. The corn seed blend of claim 1, wherein plants grown from the second corn seed type are substantially unpollinated by plants grown from the insect resistant first corn seed type, wherein "substantially unpollinated" refers to a seed assemblage produced by a refuge crop that exhibits less than 50% of its kernels or seed having the insect resistance transgene.

3. The corn seed blend of claim 1, wherein a corn ear produced by plants grown from the second corn seed type exhibits a reduced number of seeds comprising the insect resistance transgene when compared to a control corn seed blend comprising the first corn seed type comprising the insect resistance transgene and a recessive gametophyte factor allele and a second seed type lacking the insect resistance transgene and the dominant gametophyte factor allele.

4. The corn seed blend of claim 1, wherein the ratio of the first corn seed type to the second corn seed type is from about 70:30 to about 99:1.

5. The corn seed blend of claim 1, wherein the first corn seed type comprises a transgene encoding for a Bt insecticidal polypeptide.

6. The corn seed blend of claim 5, wherein the Bt insecticidal polypeptide has insecticidal activity against a corn ear feeding pest.

7. The corn seed blend of claim 6, wherein the corn ear feeding pest is selected from Western Bean cutworm, European corn borer, Fall armyworm, and Corn earworm.

8. The corn seed blend of claim 1, wherein the first corn seed type further comprises a transgene encoding for an RNAi or dsRNA molecule having insecticidal activity.

9. The corn seed blend of claim 5, wherein in the first corn seed type the insect resistance transgene encodes a pesticidal product selected from the group consisting of VIP3A, VIP3Aa, Cry1A.105, Cry2Ab, Cry1F, Cry1A, Cry1Ab, Cry1Ac, Cry34/35, Cry34/35Ab1, Cry34Ab1, Cry35Ab1, Cry3A, mCry3A, eCry3.1Ab, Cry3Bb, Dv49 dsRNA, and Dv_Snf7o.

10. The corn seed blend of any one of claims 1-9, wherein the gametophyte factor allele is selected from the group consisting of Ga1-s, Ga2-s, and Tcb1-s.

11. A method of reducing the incidence of pollination between plants grown from different seed types in a corn seed blend, the method comprising providing a corn seed blend comprising (i) a first corn seed type comprising an insect resistance transgene and (ii) a second corn seed type comprising a dominant gametophyte factor allele and lacking the insect resistance transgene, wherein the dominant gametophyte factor allele reduces pollination by pollen containing the recessive allele of that gametophyte factor when compared to a control corn seed blend comprising seed types lacking the dominant gametophyte factor allele.

12. The method of claim 11, wherein plants grown from the second corn seed type are substantially unpollinated by plants grown from the first corn seed type, wherein "substantially unpollinated" refers to a seed assemblage produced by a refuge crop that exhibits less than 50% of its kernels or seed having the insect resistance transgene.

13. The method of claim 11, wherein a corn ear produced by plants grown from the second corn seed type exhibits a reduced number of seeds comprising the insect resistance transgene when compared to a control corn seed blend comprising seed types that are cross pollination compatible.

14. The method of claim 11, wherein the ratio of the first corn seed type to the second corn seed type in the corn seed blend is from about 70:30 to about 99:1.

15. The method of claim 11, wherein the insect resistance transgene encodes a Bt insecticidal polypeptide.

16. The method of claim 11, wherein the insect resistance transgene encodes a polypeptide having insecticidal activity against a corn ear feeding pest.

17. The method of claim 11, wherein the corn ear feeding pest is selected from Western Bean cutworm, European corn borer, Fall armyworm, and Corn earworm.

18. The method of claim 17, wherein the pesticidal agent is active against *Helicoverpa zea*, and wherein the reduction in pollination occurs at the tip portion of the corn ears.

19. The method of claim 11, wherein the insect resistance transgene encodes for an RNAi or dsRNA molecule having insecticidal activity.

20. The method of claim 11, wherein the method further comprises treating the first or the second corn seed type with a formulation to delay or to accelerate the time to reproductive maturation of plants grown from the treated seed.

21. An insect resistance management method for planting a refuge crop with or alongside of a transgenic insect resistant crop, wherein the method comprises providing a corn seed blend comprising (i) a first corn seed type comprising an insect resistance transgene and a recessive gametophyte factor allele and (ii) a second corn seed type comprising a dominant gametophyte factor allele and that lacks the insect resistance transgene, wherein pollination by pollen carrying the recessive allele of that gametophyte factor is reduced compared to a control corn seed blend comprising the first corn seed type comprising the insect resistance transgene and a recessive gametophyte factor allele and a second seed type comprising the same recessive gametophyte factor allele and lacking the insect resistance transgene.

22. The insect resistance management method of claim 21, wherein pollination by recessive gametophyte factor pollen is reduced at least two-fold compared to a corn seed blend comprising a refuge seed lacking the dominant gametophyte factor allele.

23. The insect resistance management method of claim 22, wherein a corn ear produced by plants grown from the second corn seed type exhibits a reduced number of seeds comprising the insect resistance transgene when compared to a control corn seed blend comprising seed types that are cross-pollination compatible.

24. A insect resistance management method for planting a refuge crop with or alongside of a transgenic insect resistant crop, wherein the method comprises providing (i) a first corn seed type comprising an insect resistance transgene and (ii) a second corn seed type comprising a dominant gametophyte factor allele that lacks the insect resistance transgene, wherein pollination by recessive gametophyte factor pollen is reduced compared to a corn seed blend comprising a refuge seed lacking the dominant gametophyte factor allele, and wherein the second corn seed type is planted as strips or blocks in an insect resistant corn crop field, or as an adjacent field.

25. The insect resistance management method of claim 24, wherein pollination by recessive gametophyte factor pollen is reduced at least two-fold compared to a corn seed blend comprising a refuge seed lacking the dominant gametophyte factor allele.

26. The insect resistance management method of claim 25, wherein a corn ear produced by plants grown from the second corn seed type exhibits a reduced number of seeds comprising the insect resistance transgene when compared to a control corn seed blend comprising seed types that are cross-pollination compatible.

27. A insect resistance management method for ensuring compliance with government regulations for planting a refuge crop with or alongside of a transgenic crop, wherein the method comprises providing a corn seed blend comprising (i) a first corn seed type comprising an insect resistance transgene and (ii) a second corn seed type comprising a dominant gametophyte factor allele and that lacks the insect resistance transgene wherein pollination by recessive gametophyte factor pollen is reduced compared to a corn seed blend comprising a refuge seed lacking the dominant gametophyte factor allele.

28. The method of claim 27, wherein pollination by recessive gametophyte factor pollen is reduced at least two-fold compared to a corn seed blend comprising a refuge seed lacking the dominant gametophyte factor allele.

29. The method of claim 28, wherein a corn ear produced by plants grown from the second corn seed type exhibits a reduced number of seeds comprising the insect resistance transgene when compared to a control corn seed blend comprising seed types that are cross-pollination compatible.

\* \* \* \* \*